US008974628B2

(12) United States Patent
Nozawa et al.

(10) Patent No.: US 8,974,628 B2
(45) Date of Patent: Mar. 10, 2015

(54) PLASMA TREATMENT DEVICE AND OPTICAL MONITOR DEVICE

(75) Inventors: Toshihisa Nozawa, Sendai (JP); Takahiro Senda, Sendai (JP); Shinya Nishimoto, Sendai (JP); Munetaka Yamagami, Tokyo (JP); Kazuki Moyama, Sendai (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 13/818,720

(22) PCT Filed: Aug. 24, 2011

(86) PCT No.: PCT/JP2011/004698
§ 371 (c)(1),
(2), (4) Date: Mar. 27, 2013

(87) PCT Pub. No.: WO2012/026117
PCT Pub. Date: Mar. 1, 2012

(65) Prior Publication Data
US 2013/0180660 A1    Jul. 18, 2013

(30) Foreign Application Priority Data
Aug. 26, 2010   (JP) .................................. 2010-189435

(51) Int. Cl.
*C23C 16/00* (2006.01)
*C23F 1/00* (2006.01)
*H01L 21/306* (2006.01)
*G01N 21/55* (2014.01)
*H01J 37/32* (2006.01)
(Continued)

(52) U.S. Cl.
CPC .......... *G01N 21/55* (2013.01); *H01J 37/32192* (2013.01); *H01J 37/32972* (2013.01); *H01L 21/31116* (2013.01); *H01L 22/26* (2013.01); *H01L 22/12* (2013.01); *H01L 29/6659* (2013.01)

USPC ........... 156/345.24; 156/345.25; 156/345.41; 118/723 MW

(58) Field of Classification Search
USPC ......................... 156/345.24–345.28, 345.41; 118/723 MW
See application file for complete search history.

(56) References Cited

U.S. PATENT DOCUMENTS

| 4,450,031 | A  | * | 5/1984 | Ono et al. ................. 156/345.39 |
| 6,390,019 | B1 | * | 5/2002 | Grimbergen et al. ..... 118/723 R |
| 6,755,932 | B2 | * | 6/2004 | Masuda et al. ........... 156/345.24 |
| 6,870,123 | B2 | * | 3/2005 | Suzuki et al. ............ 219/121.43 |

(Continued)

FOREIGN PATENT DOCUMENTS

| CN | 1636261     |   | 7/2005 |
| CN | 101640168 A |   | 2/2010 |

(Continued)

OTHER PUBLICATIONS

International Search Report mailed Nov. 8, 2011 in PCT/JP2011/004698.

*Primary Examiner* — Rakesh Dhingra
(74) *Attorney, Agent, or Firm* — Rothwell, Figg, Ernst & Manbeck, P.C.

(57) ABSTRACT

An optical monitor device of the present microwave plasma etching device has: a monitor head located in a position more radially inward than the edge of a semiconductor wafer W mounted on a susceptor, more radially outward than a coaxial pipe, and above a cover plate; an optical waveguide for monitoring provided vertically below the monitor head, and longitudinally traversing the cooling plate, a dielectric plate, and a dielectric window; and a monitor main body optically connected to the monitor head via an optical fiber.

10 Claims, 11 Drawing Sheets

(51) Int. Cl.
*H01L 21/311* (2006.01)
*H01L 21/66* (2006.01)
*H01L 29/66* (2006.01)

(56) References Cited

U.S. PATENT DOCUMENTS

2002/0048019 A1    4/2002   Sui et al.
2006/0151430 A1*   7/2006   Yang et al. .................. 216/59
2008/0078504 A1*   4/2008   Vukovic ................. 156/345.28
2010/0029020 A1    2/2010   Saito et al.
2010/0101728 A1*   4/2010   Iwasaki .................. 156/345.33

FOREIGN PATENT DOCUMENTS

| | | |
|---|---|---|
| CN | 101647101 A | 2/2010 |
| EP | 1352415 A2 | 10/2003 |
| JP | 2004-79449 A | 3/2004 |
| JP | 2006-121072 A | 5/2006 |
| JP | 2006-190877 A | 7/2006 |
| JP | 2007-67423 A | 3/2007 |
| JP | 2008-251660 A | 10/2008 |
| JP | 2009-54997 A | 3/2009 |
| JP | 2009-152304 A | 7/2009 |
| JP | 2010-34393 A | 2/2010 |
| KR | 10-2008-0065709 A | 7/2008 |
| KR | 10-2010-0003293 A | 1/2010 |
| KR | 10-2010-0013284 A | 2/2010 |
| KR | 10-2010-0045955 A | 5/2010 |
| TW | 510008 B | 11/2002 |
| WO | 02/35586 A2 | 5/2002 |
| WO | 2008/123605 A1 | 10/2008 |

\* cited by examiner

FIG.3.A
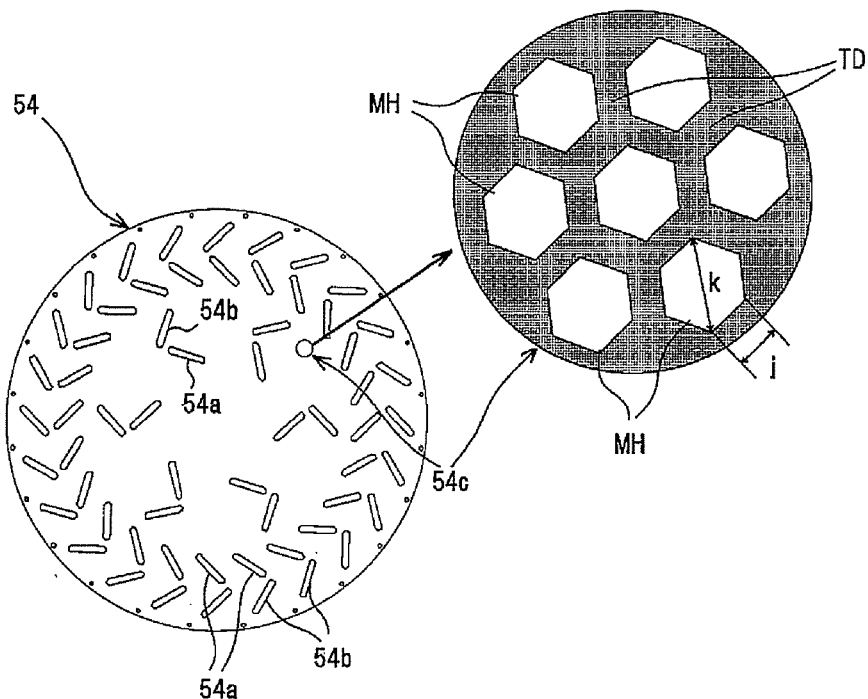
FIG.3B
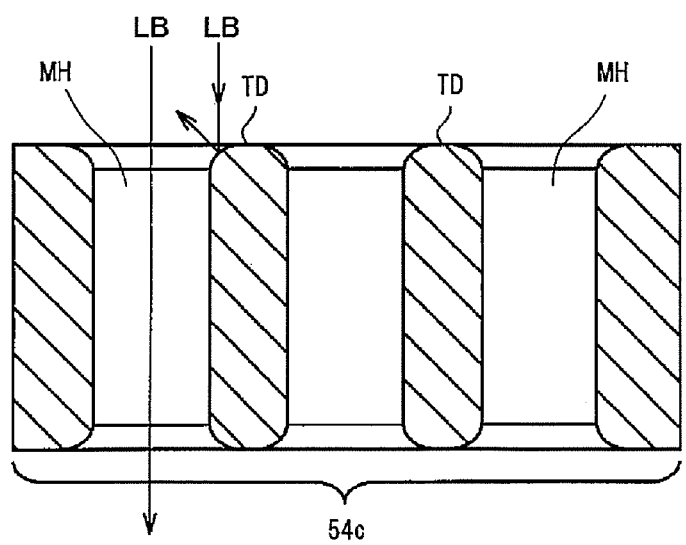

FIG.8.A
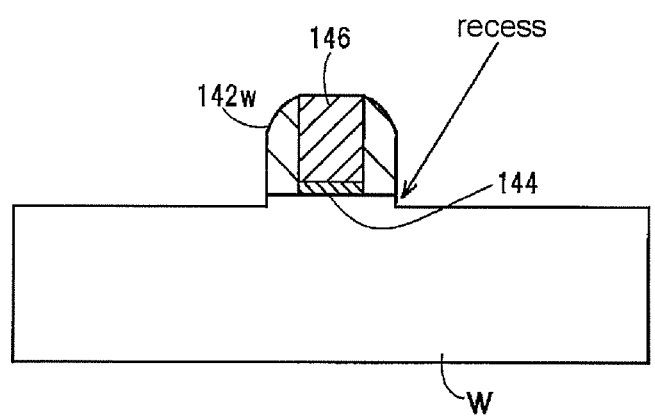
FIG.8B
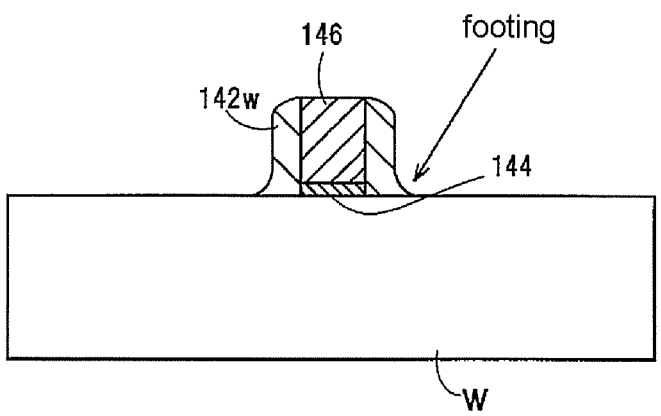

US 8,974,628 B2

PLASMA TREATMENT DEVICE AND OPTICAL MONITOR DEVICE

CROSS REFERENCE TO RELATED APPLICATIONS

This application is a 35 U.S.C. 371 National Phase Entry Application from PCT/JP2011/004698, filed Aug. 24, 2011, which claims the benefit of Japanese Patent Application No. 2010-189435, filed on Aug. 26, 2010, the disclosures of which are incorporated herein in its entirety by reference.

TECHNICAL FIELD

The present invention relates to a plasma treatment device that performs a desired treatment on a substrate to be treated using plasma generated by microwave discharge.

BACKGROUND ART

Plasma has been frequently used in, for example, etching, deposition, oxidization and sputtering of a manufacturing process of semiconductor devices and flat panel displays (FPD) for an improved reaction of the treatment gas in a relatively low temperature. Conventionally, plasma has been generated using either a high frequency discharge of MHz range or a microwave discharge of GHz range for these types of plasma processing.

Plasma generated using the microwave discharge has an advantage in that high density plasma having low electron temperature can be generated under a relatively lower pressure, and in particular, large-diameter plasma can be efficiently generated by employing a slot antenna and a planar plate shaped microwave introduction window structure. It also has an advantage in that the plasma treatment device can be simplified since a magnetic field is not needed.

In particular, a radial line slot antenna among the slot antenna radiates microwave uniformly and widely from a slot plate having multiple slots arranged concentrically. As a result, a large-diameter plasma can be generated having an excellent uniformity of density and controllability can be generated.

In the meantime, the process being performed within a treatment vessel of the microwave plasma treatment device is occasionally controlled in real time through an in-situ monitoring. When an optical monitor device is installed on the microwave plasma treatment device equipped with such a slot antenna, it may be required to configure an optical waveguide for monitoring such that the optical waveguide does not affect not only the uniformity of electromagnetic wave radiation of the slot antenna, but also the uniformity of plasma density.

In regard to this matter, the optical monitor device installed in the plasma treatment device disclosed in Patent Document 1 uses a microwave transmission line which transmits microwave generated from a microwave generator toward a treatment vessel, in which the last section of the microwave transmission line is a coaxial line which is traverse from directly above at the center of the slot antenna in a vertical direction. The internal conductor of the coaxial line is configured as a hollow tube. The process performed within the treatment vessel is adapted to be optically monitored in-situ by making light pass through the hollow tube.

The optical monitor device is formed with a hole for the optical waveguide which penetrates through the center of the slot antenna to be continued with the hollow tube (internal conductor) of the coaxial line. In general, the center of the planar plate slot antenna is the center of a radial waveguide, and even if a through hole for the optical waveguide is formed at such a place, no influence will be exerted on uniformity of the electromagnetic wave radiation of the slot antenna, and thus no trouble will be caused in uniformity or controllability of plasma density.

PRIOR ART DOCUMENT

Patent Document

Patent Document 1: Japanese Patent Laid-Open Publication No. 2008-251660

SUMMARY OF INVENTION

Problems to be Solved by the Invention

The conventional optical monitor device disclosed in Patent Document 1 has a difficulty in forming an optical waveguide for monitoring within a microwave transmission line (coaxial line). That is, the diameter of the hollow tube as the internal conductor of the coaxial line is limited in terms of a propagation mode or a characteristic impedance of electromagnetic wave. For example, an optical waveguide having a sufficiently large diameter, i.e., a sufficiently large amount of light, cannot be obtained not only in a case where laser light is used in a monitor light but also in a case non-coherent light having a wide wavelength range such as a lamp light is used as the monitor light.

Further, the conventional optical monitor device also has a restriction in that the hollow tube (internal conductor) of the microwave transmission line (coaxial line) cannot be used for a treatment gas supply path.

The present invention intends to solve the problems of the conventional technology as described above, and provides an optical monitor device and a plasma treatment device which enable high accuracy optical monitoring of the surface of a substrate to be treated in a treatment vessel using monitor light (non-coherent monitor light) having a wide wavelength range, without affecting the uniformity of the electromagnetic radiation from a planar slot antenna.

Means to Solve the Problems

A plasma treatment device according to a first aspect of the present invention includes: a treatment vessel that is capable of being evacuated and at least partly includes a dielectric window; a substrate holding unit that holds a substrate to be treated within the treatment vessel; a treatment gas supply unit that supplies a desired treatment gas within the treatment vessel in order to perform a desired plasma treatment on the substrate; a slot plate made of a conductor and having one or plural slots for radiating microwave into the treatment vessel and installed above the dielectric window; a microwave supply unit that supplies microwave into the treatment vessel through the slot plate and the dielectric window in order to generate plasma of a treatment gas by a plasma discharge; and an optical monitor unit that optically monitors or measures a surface of the substrate within the treatment vessel through a mesh shaped penetration hole formed on the slot plate and the dielectric window. The optical monitor unit includes: a light source that generates monitor light; a light receiving unit that converts reflected light from the substrate for the monitor light into an electrical signal; a monitor circuit that outputs monitor information or a monitor result by allowing the electrical signal from the light receiving unit to be subjected to a predetermined signal processing; a monitor head that irradiates the monitor light on the surface of the substrate held on the substrate holding unit through the mesh type penetration holes of the slot plate and the dielectric window, and receives the reflected light from the surface of the substrate through the mesh type penetration holes of the slot plate and the dielectric window; a monitor light transmission unit that transmits the monitor light from the light source to the monitor head; and a reflected light transmission unit that transmits the reflected light from the monitor head to the light receiving unit. And, the monitor head includes: a sealable housing that is made of a conductor and placed above the slot plate, a predetermined optical component that is located at a position where the monitor light or the reflected light passes within the housing, a purge gas supply unit that supplies a purge gas into the housing, and an exhaust unit that exhaust the gas from the inside of the housing.

A plasma treatment device according to a second aspect of the present invention includes: a treatment vessel that is capable of being evacuated and at least partly includes a dielectric window; a substrate holding unit that holds a substrate to be treated within the treatment vessel; a treatment gas supply unit that supplies a predetermined treatment gas within the treatment vessel in order to perform a predetermined plasma treatment on the substrate; a slot plate of a conductor that includes one or plural slots to radiate microwave within the treatment vessel, and is installed above the dielectric window; a microwave supply unit that supplies microwave into the treatment vessel through the slot plate and the dielectric window in order to generate plasma of the treatment gas by plasma discharge; and an optical monitor unit that optically monitors or measures a surface of the substrate within the treatment vessel through mesh type penetration holes formed in the slot plate and the dielectric window. The top surface of a light shielding portion in the region where the mesh type penetration holes of the slot plate are distributed is rounded.

A plasma treatment device according to a third aspect of the present invention includes: a treatment vessel that is capable of being evacuated and at least partly includes a dielectric window; a substrate holding unit that holds a substrate to be treated within the treatment vessel; a treatment gas supply unit that supplies a predetermined treatment gas within the treatment vessel in order to perform a predetermined plasma treatment on the substrate; a slot plate of a conductor that includes one or plural slots to radiate microwave within the treatment vessel, and is installed above the dielectric window; a microwave supply unit that supplies microwave into the treatment vessel through the slot plate and the dielectric window in order to generate plasma of the treatment gas by plasma discharge; and an optical monitor unit that optically monitors or measures a surface of the substrate within the treatment vessel through mesh type penetration holes formed in the slot plate and the dielectric window. In the dielectric window, at least a portion that is overlapped with the region where the mesh type penetration holes of the slot plate are distributed is of a synthetic quartz.

An optical monitor device for optically monitoring or measuring a surface of a substrate in a plasma treatment device according to a fourth aspect of the present invention, wherein a substrate to be treated is accommodated in a vacuum treatment vessel that is capable of being evacuated and at least partly includes a dielectric window, the substrate being held in a substrate holding unit, a treatment gas is supplied into the treatment vessel, microwave is supplied into the treatment vessel through a dielectric window and a slot plate that is made of a conductor and having one or plural slots and installed above the dielectric window, and plasma of the treatment gas is generated by a microwave discharge such that a desired plasma treatment on the substrate is performed under plasma, the optical monitor device includes: a light source that generates monitor light; a light receiving unit that converts reflected light from the substrate of the monitor light into an electrical signal; a monitor circuit that outputs monitor information or a monitor result by allowing the electrical signal from the light receiving unit to be subjected to a predetermined signal processing; a mesh type penetration holes that are formed in the slot plate in order to pass the monitor light and the reflected light from the surface of the substrate therethrough; a monitor head that irradiates the monitor light on the surface of the substrate held on the substrate holding unit through the mesh type penetration holes of the slot plate and the dielectric window, and receives the reflected light from the surface of the substrate through the mesh type penetration holes of the slot plate and the dielectric window; a monitor light transmission unit that transmits the monitor light from the light source to the monitor head; and a reflected light transmission unit that transmits the reflected light from the monitor head to the light receiving unit. A first mesh type penetration hole for passing the monitor light therethrough and a second mesh shaped penetration hole for passing the reflected light therethrough are formed on the slot plate, and the monitor head irradiates the monitor light on the surface of the substrate on the substrate holding unit through the first mesh shaped penetration hole of the slot plate and the dielectric window, and receives the reflected light from the surface of the substrate through the second mesh type penetration hole of the slot plate and the dielectric window.

An optical monitor device according to the present invention is an optical monitor device for optically monitoring or measuring surface of the substrate in a plasma treatment device in which a substrate to be treated is accommodated in a treatment vessel that is capable of being evacuated and at least a portion of ceiling plate includes a dielectric window and the substrate being held in a substrate holding unit, a treatment gas is supplied into the treatment vessel, microwave is supplied into the treatment vessel through a dielectric window and a slot plate made of a conductor and having one or plural slots and installed above the dielectric window, and plasma of the treatment gas is generated by a microwave discharge such that a desired plasma treatment on the substrate is performed under plasma, the optical monitor device includes: a light source that generates a monitor light; a light receiving unit that converts a reflective light from the substrate of the monitor light into an electrical signal; a monitor circuit that outputs a monitor information or a monitor result by allowing the electrical signal from the light receiving unit to be subjected to a predetermined signal processing; a mesh shaped penetration hole formed on the slot plate in order to pass through the monitor light and the reflective light from the surface of the substrate; a monitor head that irradiates the monitor light on the surface of the substrate held on the substrate holding unit through the mesh shaped penetration hole of the slot plate and the dielectric window and receives the reflective light from the surface of the substrate through the mesh shaped penetration hole of the slot plate and the dielectric window; a monitor light transmission unit that transmits the monitor light from the light source to the monitor head; and a reflective light transmission unit that transmits the reflective light from the monitor head to the light receiving unit.

In a microwave plasma treatment device configured as described above, microwave supplied from the microwave supply unit is radiated from the slots of the slot plate into the treatment vessel through the dielectric window and the treatment gas is dissociated by its microwave electric field to generate plasma. Plasma generated in the vicinity of the dielectric window is diffused downwardly in the treatment vessel and a desired treatment such as a micro-machining or a thin film depositing is performed under the plasma.

The optical monitor unit or the optical monitor device described above that performs an optical in-situ monitoring or measuring of the surface of the substrate to be treated that is being subjected to the plasma treatment through the optical waveguide for monitoring that passes through the conductive slot plate and the dielectric window. Here, in the slot plate, the mesh shaped penetration hole forms an optical waveguide for monitoring, while microwave supplied from the microwave supply unit smoothly propagates all of the portions of the mesh shaped penetration hole as well as the other portions other than the slots. Accordingly, it is possible to stably and securely carry out a desired optical monitoring on a surface of the substrate to be treated with high accuracy by constructing an optical waveguide which is appropriate for propagating monitor light (in particular, non-coherent monitor light) having a wide wavelength range, without affecting the uniformity of the electromagnetic radiation (further, uniformity of plasma density).

Effect of the Invention

According to an optical monitor device and a plasma treatment device of the present invention, with the above-described configuration and effect, it is possible to carry out high accuracy optical monitoring of the surface of a substrate to be treated in a treatment vessel using monitor light (in particular, non-coherent monitor light) having a wide wavelength range, without affecting the uniformity of the electromagnetic radiation from a planar slot antenna.

BRIEF DESCRIPTION OF DRAWINGS

FIG. 3A is a plan view illustrating a configuration of mesh type penetration holes which are formed in a slot plate in order to configure the optical waveguide in the optical monitor device of the embodiment.

FIG. 3B is a cross-sectional view illustrating a cross-sectional structure of a light shielding unit in an area where the mesh type penetration holes of the slot plate are distributed.

FIG. 8A is view illustrating an example (recess) of a bad etch-back result in forming the sidewall of the LDD structure.

FIG. 8B is view illustrating an example (footing) of bad etch back result in forming the sidewall of the LDD structure.

DETAILED DESCRIPTION

Hereinafter, exemplary embodiments of the present invention will be described with reference to the accompanying drawings.

Figure 1:
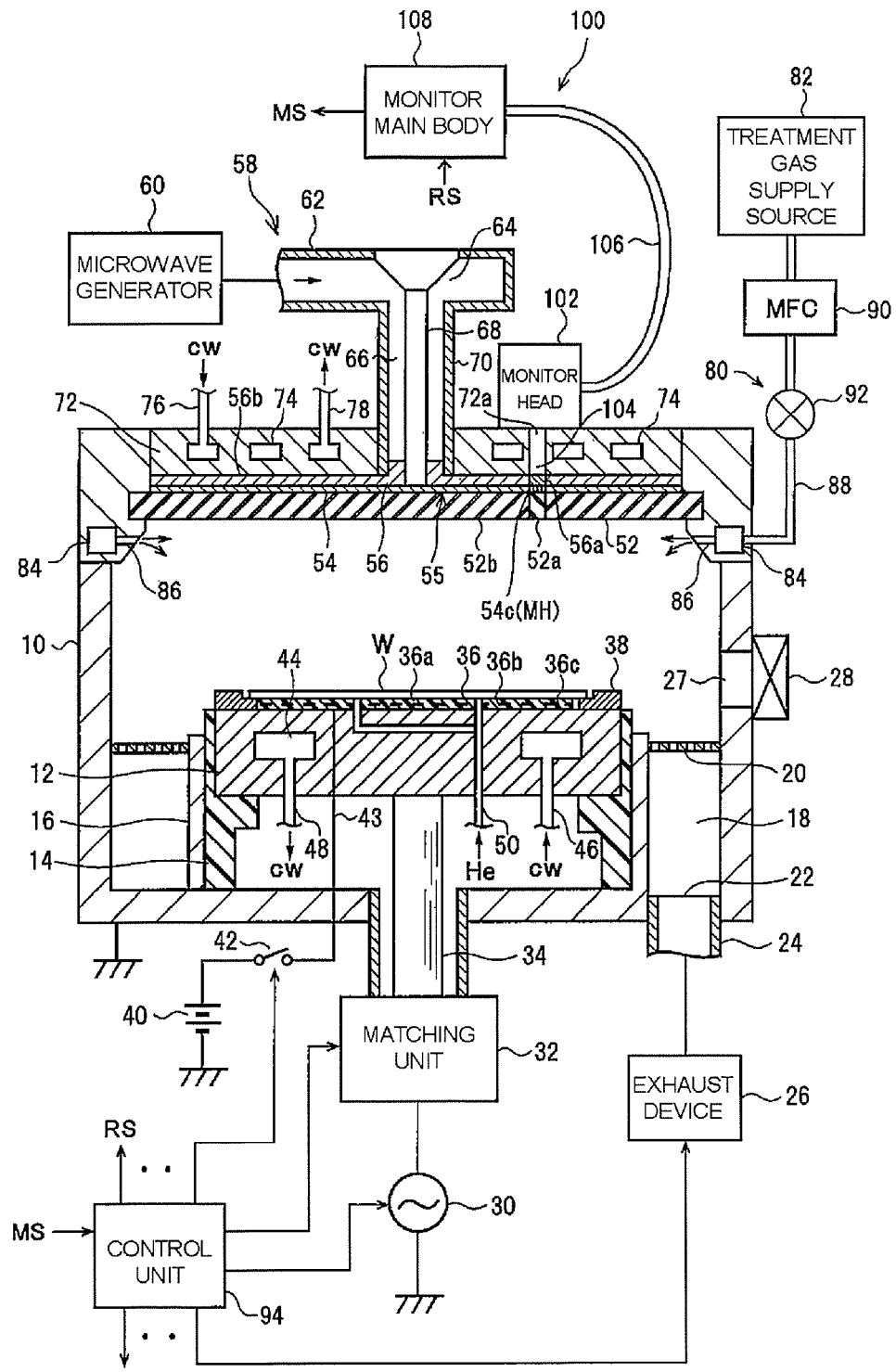
FIG. 1 is a view illustrating a configuration of a microwave plasma treatment device according to an embodiment of the present invention.

FIG. 1 illustrates a configuration of a microwave plasma treatment device according to an embodiment of the present invention. The microwave plasma treatment device is configured as a planar plate shaped surface wave excited microwave plasma etching device using a planar plate slot antenna and has a cylindrical vacuum chamber (treatment vessel) 10 made of a metallic material, for example, an aluminum or a stainless steel. Chamber 10 is protectively grounded.

First, a configuration of each component of the microwave plasma etching device that is irrelevant to generation of plasma will be described.

A disc-shaped susceptor 12 on which a substrate to be treated, for example, a semiconductor wafer W is mounted is disposed horizontally, as a substrate holding table which also serves as a high frequency electrode, at the center of a lower portion within chamber 10. Susceptor 12 is made of, for example, aluminum, and is supported by an insulating cylindrical support unit 14 which extends vertically upward from the bottom of chamber 10.

On the outer periphery of a cylindrical support unit, an annular exhaust path 18 is formed between a conductive cylindrical support unit 16 which extends vertically upward from the bottom of chamber 10 and an inner wall of chamber 10. An annular baffle plate 20 is attached to an upper portion or inlet of exhaust path 18 and one or plural exhaust ports 22 are installed on the bottom portion of exhaust path 18. An exhaust device 26 is connected to each exhaust port 22 through an exhaust pipe 24. Exhaust device 26 includes a vacuum pump such as a turbo molecular pump so that a plasma treatment space within chamber 10 can be decompressed to a desired vacuum level. A gate valve 28 which opens and closes a carry-in and carry-out port 27 of semiconductor wafer W is attached to the outside of the sidewall of chamber 10.

A high frequency power supply 30 for RF biasing is electrically connected to susceptor 12 through a matching unit 32 and a power feeding rod 34. High frequency power supply 30 outputs a predetermined frequency, for example, a high frequency of 13.56 MHz, which is suitable for controlling ion energy input to the semiconductor wafer W, with a predetermined power. Matching unit 32 accommodates a matcher for performing a matching between an impedance of high frequency power supply 30 side and an impedance of a load (mainly, electrode, plasma, chamber) side, a blocking condenser for generating self-bias is included in the matcher.

An electrostatic chuck 36 for holding semiconductor wafer W using an electrostatic adsorbing force is installed on an upper surface of susceptor 12 and a focus ring 38 annularly surrounding the periphery of the semiconductor wafer W is installed in the radially outside of electrostatic chuck 36. Electrostatic chuck 36 is configured in such a manner that an electrode 36a including a conductive film is sandwiched between a pair of insulating films 36b and 36c. A high voltage direct power supply 40 is electrically connected to electrode 36a through a switch 42 and a sheathed line 43. Semiconductor wafer W is adsorbed and held on the electrostatic chuck 36 by an electrostatic force by a direct voltage applied form direct power supply 40.

An annular refrigerant chamber 44 extending, for example, in a circumferential direction is installed inside susceptor 12. A refrigerant having a predetermined temperature, for example, cooling water cw is supplied to refrigerant chamber 44 from a chiller unit (not illustrated) through pipes 46 and 48. A treatment temperature of semiconductor wafer W mounted on electrostatic chuck 36 can be controlled by a temperature of the refrigerant. Further, a heat transfer gas, for example, He gas, from a heat transfer gas supply unit (not illustrated) is supplied between the top surface of electrostatic chuck 36 and the rear surface of semiconductor wafer W through a gas supply pipe 50. Further, for loading/unloading of semiconductor wafer W, a lift pin, an elevating mechanism thereof (not illustrated) and the like that may be moved up and down vertically through susceptor 12 are installed.

Next, a configuration of each component of the microwave plasma etching device that is relevant to generation of plasma will be described.

A circular dielectric window 52 for introducing microwave is hermitically attached to a ceiling surface opposed to susceptor 12 of chamber 10 as a ceiling plate. As will be described in detail below, dielectric window 52 is configured such that a portion 52a through which an optical waveguide 104 for monitoring passes is formed of a synthetic quartz having a high transmittance to light (in particular, ultraviolet ray) of a short wavelength and other portion 52b is formed of an inexpensive fused quartz.

A planar plate-shaped slot antenna, for example, a disc-shaped radial line slot antenna 55 is installed above dielectric window 52. Radial line slot antenna 55 is configured by a slot plate 54, a dielectric plate (a delay plate) 56 and a metal portion of the upper surface of the dielectric plate (lower surface of a cover plate 72).

Slot plate 54 includes, as illustrated in FIG. 3A, multiple slot pairs 54a, 54b concentrically distributed as slots for radiating microwave. Further, as will be described in detail below, a mesh type penetration (gap) holes MH are formed at a portion 54c of slot plate 54 through which optical waveguide 104 for monitoring passes.

Radial line slot antenna 55 is electromagnetically connected to microwave transmission line 58 through dielectric plate 56 installed above slot plate 54. Dielectric plate 56 is configured such that a portion 56a through which optical waveguide 104 for monitoring passes is formed of a synthetic quartz having a high transmittance to light (in particular, ultraviolet ray) of a short wavelength. Other portion 56b of dielectric plate 56 is formed of a dielectric material having high dielectric constant, which is appropriate for compressing (shortening) the wavelength of microwave, for example, a quartz, an aluminum oxide or an aluminum nitride. Here, like dielectric window 52, other portion 56b is formed of the inexpensive fused quartz.

Microwave transmission line 58 is a line which transmits microwave, for example, microwave of 2.45 GHz, which is output with a predetermined power from a microwave generator 60 to radial line slot antenna 55, and includes a waveguide 62, a waveguide-coaxial pipe converter 64 and a coaxial pipe 66. Waveguide 62 is, for example, a rectangular waveguide, and transmits microwave from the microwave generator 60 using a TE mode as a transmission mode to waveguide-coaxial pipe converter 64 toward chamber 10.

Waveguide-coaxial pipe converter 64 connects a terminating end portion of waveguide 62 with a starting end portion of coaxial pipe 66 to convert a transmission mode of quadrangle waveguide 62 into a transmission mode of coaxial pipe 66. Coaxial pipe 66 extends vertically downwardly from waveguide-coaxial pipe converter 64 to a central portion of the top surface of chamber 10, and an end portion or lower end portion of the coaxial line thereof is connected to the central part of slot plate 54 through dielectric plate 56. Coaxial pipe 66 is configured in a cylindrical body, and microwave is propagated through a space between internal conductor 68 and an external conductor 70 in a TEM mode.

Microwave output from microwave generator 60 is propagated through waveguide 62, waveguide-coaxial pipe converter 64 and coaxial pipe 66 of the above-described microwave transmission line 58 and is fed to dielectric plate 56 of radial line slot antenna 55. In the meantime, microwave expanded in a radial direction while being shortened in its wavelength within dielectric plate 56 becomes a planar surface wave which is circularly polarized wave which includes two polarized wave components orthogonal to each other, and is radiated towards the inside of chamber 10. Microwave radiated into chamber 10 ionizes neighboring gas, thereby generating high density plasma with a low electron temperature. In the meantime, electric field of microwave (electric field of surface wave) propagates in a radial direction along the surface of dielectric window 52 and plasma.

A cover plate 72 which also serves as a rear plate of the antenna is installed above the dielectric plate 56 to cover the top surface of chamber 10. Cover plate 72 is made of, for example, an aluminum, and has a function of absorbing heat (heat dissipating) of dielectric loss generated from dielectric window 52 and dielectric plate 56 or heat generated according to a process, thereby adjusting the temperature thereof to a certain temperature. For this cooling function, a refrigerant having a predetermined temperature, for example cooling water cw is circularly provided to a flow path 74 formed in the inside of cover plate 72 from a chiller unit (not illustrated) through pipes 76 and 77. A hole 72a which vertically penetrating the surface of the plate is formed at a portion of cover plate 72 through which optical waveguide 104 for monitoring passes.

Treatment gas supply unit 80 includes a treatment gas supply source 82 located in the outside of chamber 10, a manifold or a buffer chamber 84 formed in an annular shape within the sidewall of chamber 10 at a position slightly lower than dielectric window 52, a plurality of sidewall gas ejection ports 86 formed at equal intervals in the circumferential direction and extending from buffer chamber 84 to a plasma generation space, and a gas supply pipe 88 extending from the treatment gas supply source 82 to the buffer chamber 84. A mass flow controller (MFC) 90 and an opening/closing valve 92 are installed in the way of gas supply pipe 88.

In treatment gas supply unit 80, the treatment gas delivered in a predetermined flow rate from treatment gas supply source 82 is introduced into buffer chamber 84 in the inside of the sidewall of chamber 10 through gas supply pipe 88, uniformized in pressure in the circumferential direction within buffer chamber 84, and then ejected substantially horizontally from sidewall gas ejection ports 86 towards the center of chamber 10 to be diffused into the plasma generation space.

A controller 94 includes a microcomputer, and controls the operation of each component within the plasma etching device, for example, an exhaust device 26, a high frequency power supply 30, a switch 42 for electrostatic chuck 36, a microwave generator 60, treatment gas supply unit 80, a heat transfer gas supply unit (not illustrated), and a optical monitor device 100 to be described below, and the overall operations of the device.

In the microwave plasma etching device, for performing etching, first, gate valve 28 is set to be in the open state, and a semiconductor wafer W to be processed is carried into chamber 10 and mounted on electrostatic chuck 36. Next, gate valve 28 is set to be in the closed state and then a treatment gas, i.e., an etching gas (typically, a mixed gas) is introduced into chamber 10 at a predetermined flow rate from treatment gas supply unit 80. Further, a heat transfer gas (He gas) is supplied to a contact interface between electrostatic chuck 36 and semiconductor wafer W from the heat transfer gas supply unit and turns ON switch 42 to confine the heat transfer gas in the contact interface using electrostatic force of electrostatic chuck 36. Then, microwave generator 60 is turned ON and propagates microwave which is output with a predetermined power from microwave generator 60 through transmission line 58 to supply power to radial line slot antenna 55 and radiates microwave from radial line slot antenna 55 into chamber 10. Further, high frequency power supply 30 is turned ON and outputs the high frequency power for RF biasing with a predetermined power to apply the high frequency to susceptor 12 through matching unit 32 and power feeding rod 34.

The etching gas introduced into chamber 10 from sidewall gas ejection ports 86 of the treatment gas supply unit 80 is diffused below dielectric window 52 and gas particles are ionized by electric field of microwave, thereby generating surface wave excited plasma. When plasma is generated, the microwave becomes surface wave which propagates in a radial direction along the lower surface of dielectric window 52 (surface opposed to the plasma) and plasma. By doing this, plasma generated below dielectric window 52 is diffused downwardly so that an isotropic etching using radicals contained in plasma and vertical etching using ion irradiation are performed on a film to be processed on the main surface of semiconductor wafer W.

The microwave plasma etching device includes an optical monitor device 100 to optically monitor a situation of the etching process performed within chamber 10, for example, a film thickness of a film to be processed which is reduced as time elapses, in-situ or in real time.

Optical monitor device 100 is installed at a position located more radially inward than the edge of semiconductor wafer W mounted on susceptor 12, and more radially outward than coaxial pipe 66. Optical monitor device 100 has a monitor head 102 located above cover plate 72, an optical waveguide 104 for monitoring, and a monitor main body 108 optically connected to monitor head 102 via an optical fiber 106. Optical waveguide 104 for monitoring is formed vertically below monitor head 102 to traverse cover plate 72, dielectric plate 54, and dielectric window 52.

Figure 2:
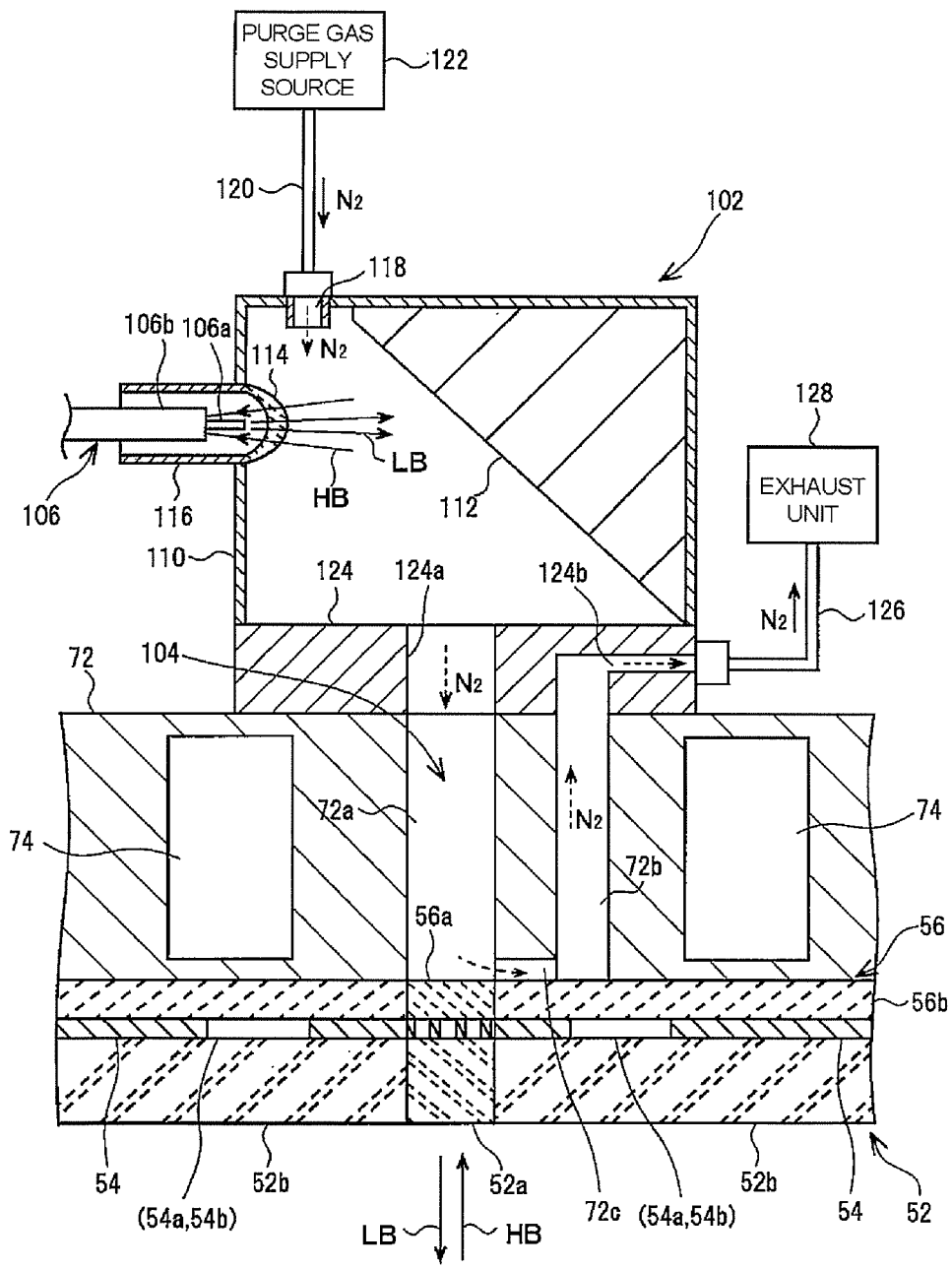
FIG. 2 is a cross sectional view illustrating a configuration of an optical waveguide and a monitor head of an optical monitor device according to an embodiment installed in the microwave plasma treatment device of FIG. 1.

FIG. 2 illustrates a configuration of monitor head 102 and optical waveguide 104. Monitor head 102 has a sealable cap type housing 110 made of a conductor, for example, an aluminum and is provided with, for example, an optical reflector 112 and an optical lens 114 as optical components for monitoring.

Optical reflector 12 is made of, for example, an aluminum, and has an inclined surface of about 45 degrees which inclined downwardly to be opposed to an end surface of optical fiber 106 which traverses the inside of the housing 110. Monitor light LB exited horizontally from optical fiber 106 is reflected vertically downward by optical reflector 112 to pass through optical waveguide 104 to be incident on semiconductor wafer W located directly below optical waveguide 104. In the meantime, reflected light HB which exited vertically upward the semiconductor wafer W onto which the monitor light LB is irradiated comes into contact with optical reflector through optical waveguide 104, and is reflected horizontally from optical reflector 112 to be incident on optical fiber 106.

Optical lens 114 radiates monitor light LB exited from optical fiber 106 toward optical reflector 112 at a predetermined diffusion angle and collects reflected light HB from the optical reflector 112 to be received into optical fiber 106. As illustrated, optical lens 114 may be attached integrally to the front end of optical fiber 106, or may be separated from optical fiber 106 and located at a predetermined position.

Optical fiber 106 includes, for example, a twin fan-out (FO) cable, in which an inner outbound cable 106a that transmits monitor light LB and an outer inbound cable 106b that transmits reflected light HB are integrally bound. Monitor light LB exits from the end surface of inner outbound cable 106a and reflected light HB is incident on the end surface of outer inbound cable 106b. Optical fiber 106 is accommodated in a sleeve 116 which is made of a conductor, for example, aluminum, hermetically attached to housing 110, thereby being connected to monitor head 102.

The inside of monitor head 102 is electromagnetically shielded from outside by housing 110 and sleeve 116 made of the conductor as described above. Accordingly, even if microwave enters monitor head 102 from dielectric plate 56 or radial line slot antenna 55 via optical waveguide 104, the microwave will not leak out to the outside of monitor head 102.

The inner space of monitor head 102 is blocked from atmospheric space and is always purged by a purge gas, for example, $N_2$ gas, introduced from a purge gas supply port 118 provided on upper surface of housing 110. Here, purge gas supply port 118 is connected to a purge gas supply source 122 through a purge gas supply pipe 120.

In the embodiment, a base plate 124 having a thick thickness and made of a conductor, for example, an aluminum, is hermetically installed on the bottom of monitor head 102 in order to sufficiently perform the purging of the inside of monitor head 102. A through hole 124a which is continued with a through hole 72a of cover plate 72 and an exhaust flow path 124b which is continued with an exhaust flow path 72b of cover plate 72 are provided at portion of base plate 124 where the optical waveguide 104 passes. The outlet of exhaust flow path 124b is connected to, for example, an exhaust unit 128 including an exhaust fan through an exhaust tube 126. Through hole 72a and exhaust flow path 72b that constitute optical waveguide 104 are connected with each other through a communication path 72c formed at a lower end in cover plate 72.

The purge gas ($N_2$ gas) supplied from purge gas supply port 118 into the housing is filled in housing 110 and then flows through a sealed space that is formed by through hole 124a of base plate 124, through hole 72a of cover plate 72, communication path 72c, exhaust flow path 72b and exhaust flow path 124b of base plate 124 in this order and then is exhausted to the outside of exhaust unit 128.

Optical monitor device 100 in the embodiment does not use coherent laser light having a single wavelength but uses non-coherent lamp light having multiple wavelengths having, for example, a wide range of 185 nm to 785 nm as monitor light LB for monitoring the thickness of the film to be processed on semiconductor wafer W. Here, since a short wavelength (in particular, 200 nm or less) included in monitor light LB is easily absorbed into oxygen, it is significantly reduced when being exposed to the atmosphere.

In the embodiment, as described above, since a space in monitor head 102 and also a space of optical waveguide 104 for monitoring are always purged by the purge gas ($N_2$ gas), monitor light LB after exited from optical fiber 106 and also reflected light HB before received by optical fiber 106 are not contacted with the atmosphere. Therefore, monitor light LB and reflected light HB are difficult to be attenuated. Accordingly, optical monitor device 100 improves the monitoring precision.

Further, in making the monitoring precision of optical monitor device 100 and the uniformity of the electromagnetic radiation characteristic of radial line slot antenna 55 be compatible, the configuration in which the mesh type penetration holes MH are formed at a portion or an area 54c of slot plate 54 through which optical waveguide 104 for monitoring passes is also very important.

As illustrated in FIG. 3A, penetration holes MH having a predetermined shape and size are distributed within optical waveguide passing area 54c (mesh) of slot plate 54 at a predetermined density. In increasing the monitoring precision, it is preferable to increase the aperture ratio of mesh 54c. The aperture ratio of 70% or more is preferable. Here, it is preferable to form the opening of each of the penetration holes MH in a polygonal shape rather than a circular shape in order to increase the aperture ratio of mesh 54c. An opening of a regular hexagonal shape, i.e., mesh 54c with a honeycomb structure is most preferable.

According to the honeycomb structure, for example, assuming that the length of one side of each penetration hole MH is j mm, the length of the diagonal line of each penetration hole is k mm, the aperture ratio is 76.3% when j=1.0 mm and k=1.73 mm, and the aperture ratio is 71.8% when j=0.8 mm, k=1.39. However, when j=0.5 mm and k=0.89 mm, the aperture ratio is reduced to 60.3%.

Like this, in optical waveguide passing area 54c (mesh) of slot plate 54, the larger aperture ratio can be obtained as the dimension of the penetration holes MH increases. However, there is an upper limit in the opening dimension of the penetration holes MH in order to reduce the leakage of microwave from the mesh. Generally, when the opening dimension of penetration holes MH is one tenth or less of wavelength within the dielectric window, the leakage of microwave is significantly reduced. For example, when using a quartz plate as a material of dielectric window 52, a wavelength of microwave (2.45 GHz) within the quartz is 61 mm. Therefore, the opening dimension of the penetration holes MH of 6 mm or less is preferable.

In the meantime, in the dimension of the opening of the pair of slots 54a and 54b for radiating microwave, for example, the longer side is 36 mm and the shorter side is 6 mm.

In the present embodiment, optical waveguide passing area (mesh) 54c is provided to be separated from coaxial pipe 66 of microwave transmission line 58. As a result, the bore of optical waveguide passing area (mesh) 54c may be selected to have any size selected in a range where the bore does not affect the uniformity of electromagnetic wave radiation characteristic of radial line slot antenna 55, and typically may be selected to have a size in the range of about 10 mm to 20 mm.

As an additional feature to mesh shaped penetration holes MH, the present embodiment forms rounded convex surfaces on the top side of a grid part or light shielding part TD that separates penetration holes MH that are adjacent to each other in the optical waveguide passing area 54c, as illustrated in FIG. 3B. If the top side of light shielding unit TD is formed with convex surfaces, monitor light LB incident on the convex surfaces from the directly upper side is reflected obliquely rather than vertically upward. Therefore, the stray light may be reduced. The stray light returns from light shielding unit TD to monitor head 102, thereby causing the reduction of S/N ratio. This also significantly contributes to the increase of the monitoring precision of optical monitor device 100.

Figure 4:
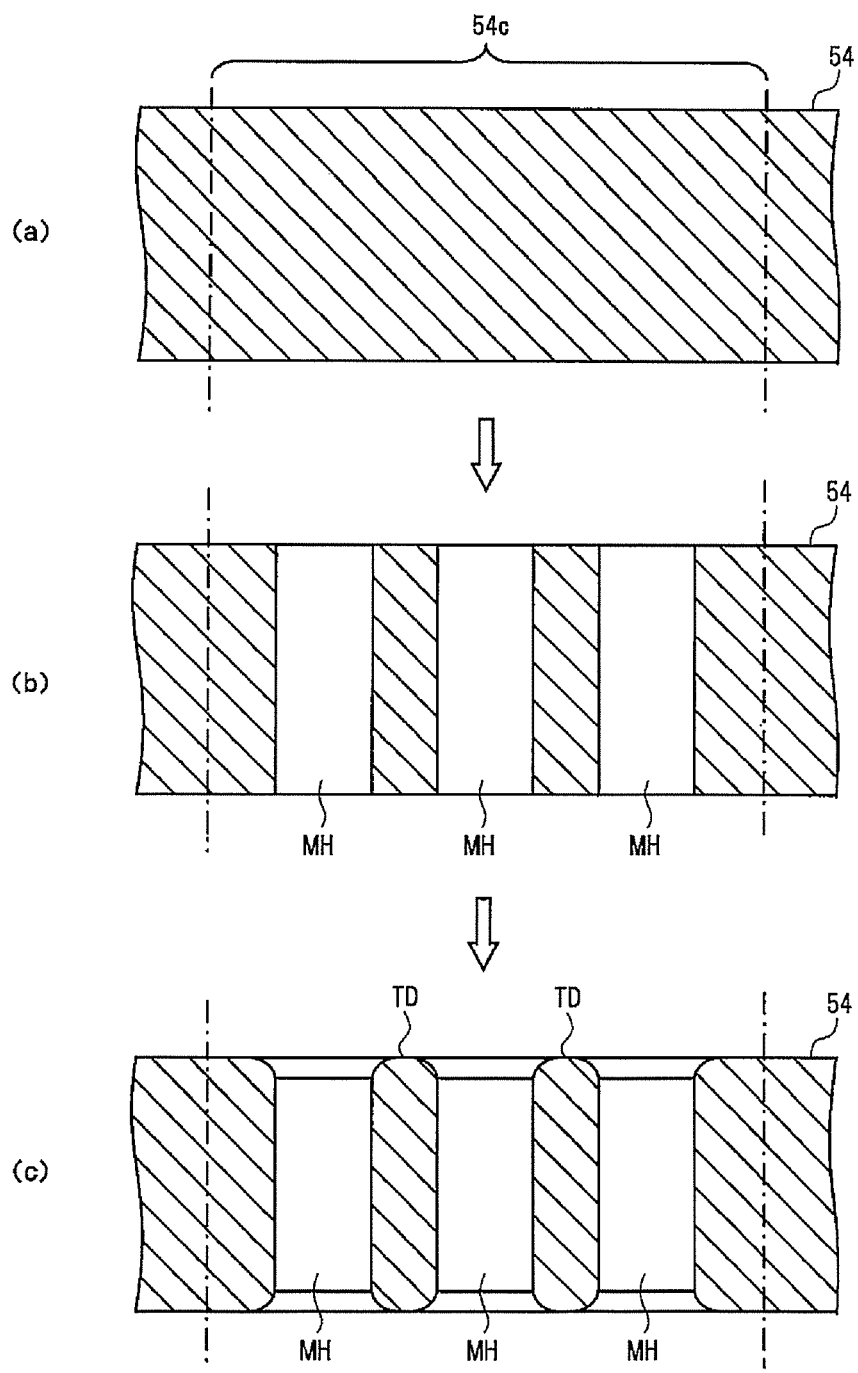
FIGS. 4 (a)-(c) are views illustrating a sequence of a method of fabricating the mesh type penetration holes in the slot plate.

FIGS. 4 (a)-(c) illustrate a method suitable for fabricating mesh type penetration holes MH in slot plate 54. In the meantime, the material of slot plate 54 is preferably a conductor such as, for example, a copper or an iron-nickel alloy, where the surface of the conductor is plated with gold in order to secure a good electrical conductivity. In particular, the iron-nickel alloy with a low linear coefficient of expansion may suppress the displacement of the slot plate.

First, as illustrated in FIGS. 4(a) and 4(b), mesh type penetration holes MH are formed in optical waveguide passing area 54c set on slot plate 54 by, for example, punching. In this step, the grid part of optical waveguide passing area 54c still has a flat surface. Subsequently, when the optical waveguide passing area 54c of slot plate 54 is immersed into an etching liquid, as illustrated in FIG. 4(c), optical waveguide passing area 54c is rounded off from the corner of the edge of each penetration hole MH and consequently, the entirety of the top side of the grid part is rounded off, thereby forming the convex surfaces. A chemical liquid containing, for example, an oxidizer, an inorganic salt and chloride ions may be used as the etching liquid. Also, the surface of the grid part or light shielding part TD may be rounded off to form convex surfaces also on the rear side of optical waveguide passing area 54c. However, even if the rear side is not rounded off (even if the rear side is a flat surface), there will be no specific problem.

In optical monitor device 100 of the present embodiment, as described above, the mesh type penetration holes MH are formed in slot plate 54 of the conductor in order to pass optical waveguide 104 for monitoring through slot plate 54. Therefore, microwave smoothly propagates through the portion of mesh shaped penetration holes MH in the radial direction (without leaking out) similarly to the other portions of the slot plate except for the pair of slots 54a and 54b. Accordingly, it is possible to construct an optical waveguide 104 for monitoring that is appropriate for propagating the non-coherent monitor light having a wide range (multiple wavelengths) without affecting the uniformity of electromagnetic wave radiation characteristic (and further the uniformity of plasma density) of radial line slot antenna 54. The degree of freedom for positioning optical waveguide passing area (mesh) 54c on slot plate 54 is high. Basically, optical waveguide passing area (mesh) 54c may be formed at any position which is located in the outside coaxial pipe 66 in the diametrical direction and where optical waveguide passing area does not interfere with the pair of slots 54a and 54b.

Also, in optical monitor device 100, as described above, portions 52a and 56a where optical waveguide 104 for monitoring passes are formed of the synthetic quartz having a high transmittance to light (in particular, ultraviolet ray) of a short wavelength. Therefore, the monitoring precision for a film thickness using the non-coherent monitor light LB including multiple wavelengths having a wide range of, for example, 185 nm to 785 nm and reflected light HB may be further improved.

Figure 5:
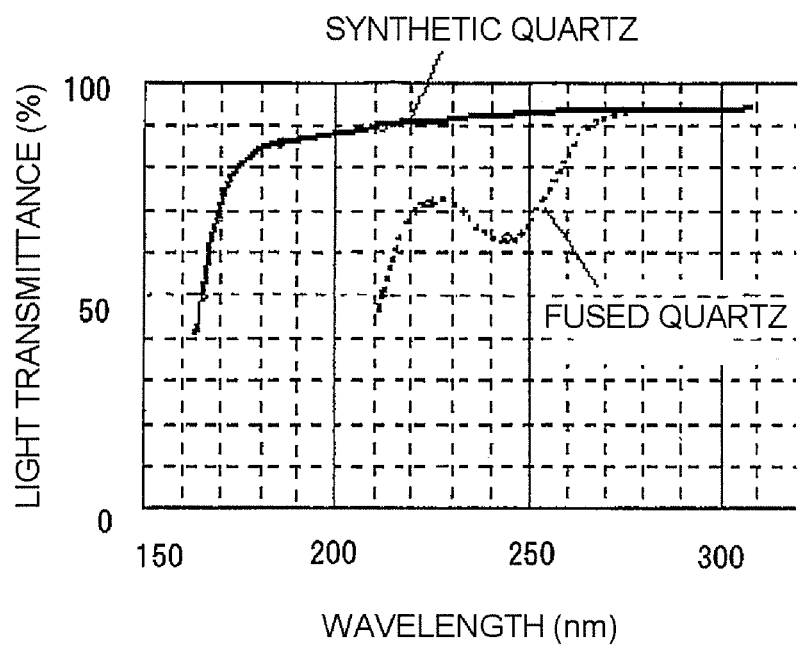
FIG. 5 is a view illustrating a wavelength dependency of light transmittance of a synthetic quartz and a fused quartz.

FIG. 5 illustrates a wavelength dependency of light transmittance of a synthetic quartz and a fused quartz. As illustrated, the light transmittance of the fused quartz is 90% or more in the wavelength region of 270 nm or more. However, when the wavelength is shorter than 270 nm, the light transmittance is reduced. In particular, when the wavelength is shorter than 200 nm, the light transmittance is significantly (50% or less) reduced. In connection with this, the light transmittance of the synthetic quartz falls within the range of 85% to 92% over the entire wavelength range (185 nm to 785 nm) of monitor light LB and reflected light HB. Therefore, the homogeneity is high and stable.

The high price is a disadvantage of the synthetic quartz. However, in the present embodiment, the synthetic quartz is used locally only in portions 52a and 56a where optical waveguide 104 for monitoring passes through. In particular, since in dielectric window 52 with the large thickness (volume), the most area 52b except for area 52a in optical waveguide 104 is formed of the inexpensive fused quartz, the cost will not be increased. Also, for dielectric plate 56, the cost will not be increased.

In the meantime, in dielectric window 52, the boundary between fused quartz portion 52b and synthetic quartz portion 52a may be vacuum sealed by, for example, welding. In dielectric plate 56, since vacuum sealing is not required, it would be sufficient if a small disc 56a made of the synthetic quartz and having a diameter of optical waveguide 104 is inserted into a circular hole formed in a plate body 56b made of the fused quartz in order to pass optical waveguide 104 for monitoring through dielectric plate 56.

Figure 6:
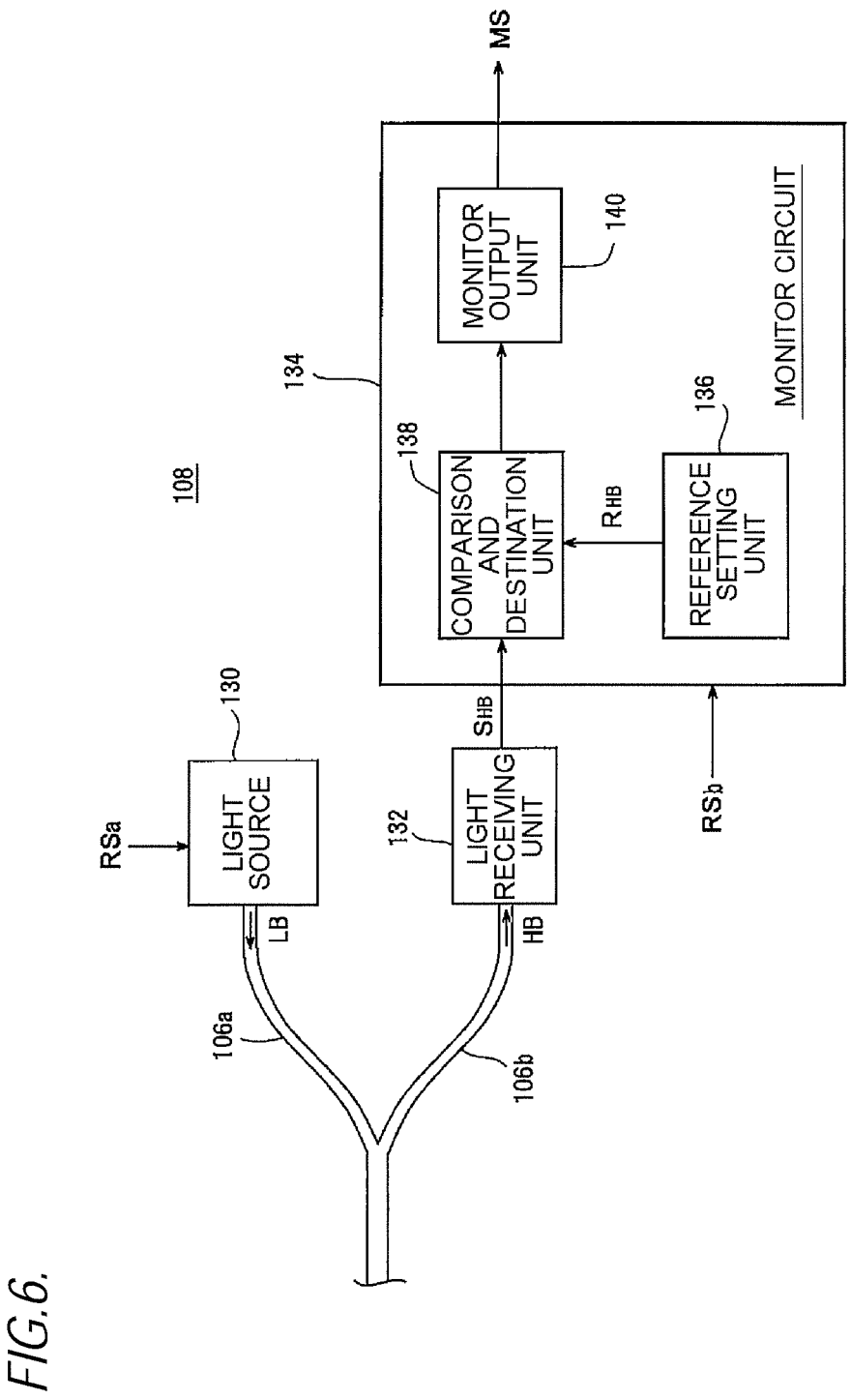
FIG. 6 is a block diagram illustrating an internal configuration of a monitor body of the optical monitor device.

FIG. 6 illustrates an example of a configuration of the inside of monitor body 108. In the present embodiment, optical monitor device 100 is provided with a light source 130, a light receiving unit 132 and a monitor circuit 134 in monitor main body 108 in order to perform in-situ monitoring of the thickness of a film to be processed on the surface of semiconductor wafer W.

Light source 130 has, for example, a halogen lamp or a xenon lamp, and generates the monitor light LB having multiple wavelengths of at least in the range of 185 nm to 785 nm. Light source 130 is optically connected to outbound cable 106a of optical fiber 106 through an optical lens which is not illustrated and is turned ON (lighting-up) and OFF (lighting-out) according to a control signal RSa from control unit 94.

Light receiving unit 132 has, for example, a photoelectric conversion element and, divides reflected light HB from the surface of semiconductor wafer W which is sent through inbound cable 106b of the optical fiber into multiple spectrums in the range of 185 nm to 785 and generates an electric signal (a reflection ratio signal $S_{HB}$) indicating the strength of the reflected light, i.e., reflection ratio, for each spectrum.

Monitor circuit 134 has a reference setting unit 136, a comparison and destination unit 138 and a monitor output unit 140. Reference setting unit 136 assigns a reference value or reference data $R_{HB}$ included in various setting values RSb given from the control unit 94 to comparison and destination unit 138. In a case of monitoring a film thickness, reference data $R_{HB}$ gives a setting value or a reference value in relation to a predetermined attribute of a spectrum reflection ratio signal $S_{HB}$ obtained from light receiving unit 132.

Comparison and destination unit 138 compares (collates) spectrum reflection ratio signal $S_{HB}$ received from light receiving unit 132 with reference data $R_{HB}$, and when the values or characteristics of the attributes predetermined between the $S_{HB}$ and the $R_{HB}$ are coincided or approximated with each other, comparison and destination unit 138 outputs monitor information or a monitor result indicating that the film thickness of film to be processed of the surface of the semiconductor wafer W reaches a setting value (or reaches the setting value after time determined by anticipation). Then, a monitor signal MS indicating such a meaning is output from monitor output unit 140 and control unit 94 (FIG. 1) causes the etching process to be stopped or switched in response to monitor signal MS.

As an example of the etching process to which the film thickness monitoring function of optical monitor device 100 of the present embodiment may be appropriately applied, there is an etch back process that forms a sidewall for a lightly doped drain (LDD) structure or a very shallow junction structure during an MOS transistor manufacturing process.

Figure 7:
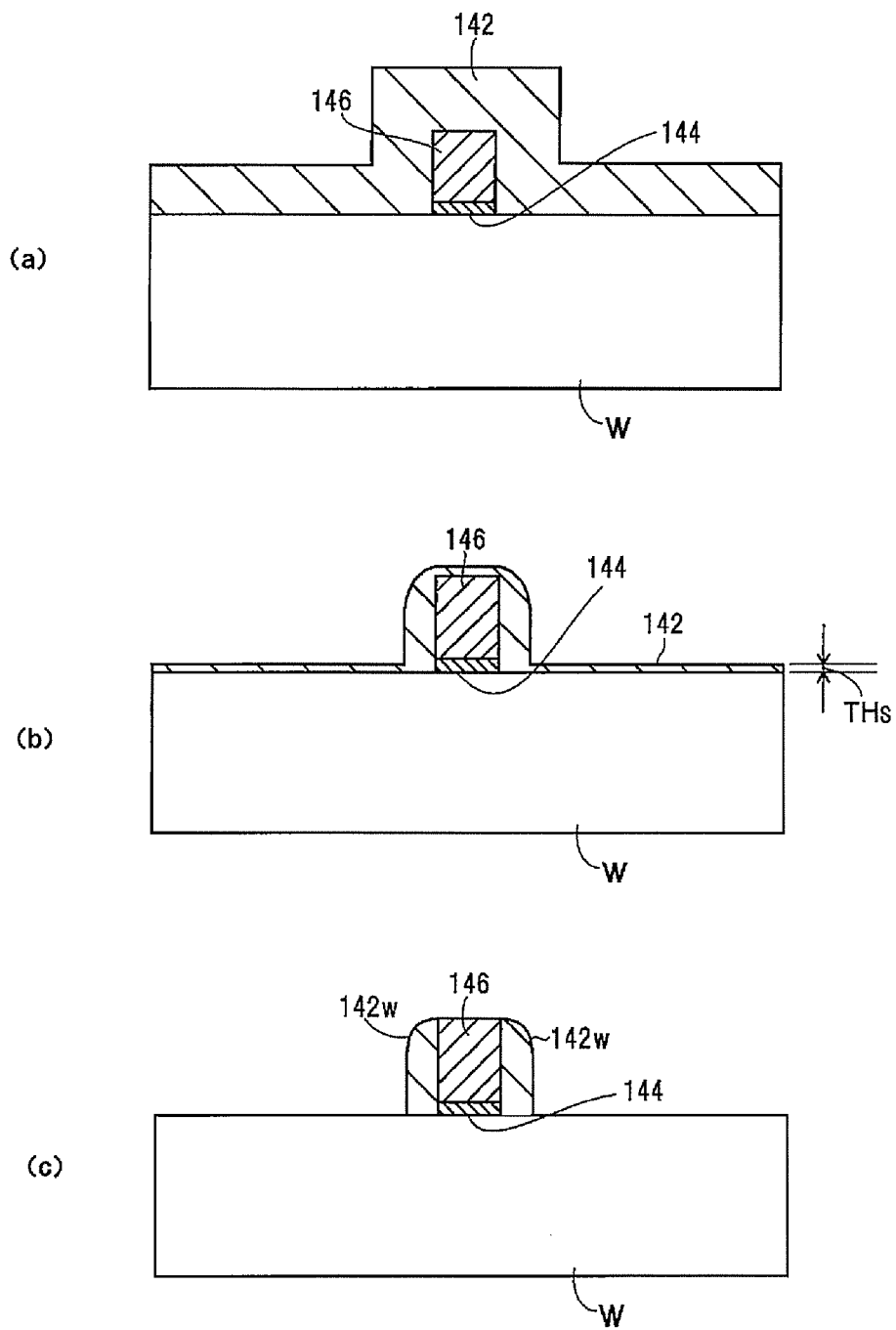
FIGS. 7 (a)-(c) are views illustrating a sequence of an etch-back process carried out to form a sidewall of an LDD structure using the plasma treatment device of FIG. 1.

FIGS. 7(a)-(c) illustrate the sequence of the etch back process in the present embodiment. In the meantime, prior to the etch back process, as illustrated in FIG. 7(a), an $SiO_2$ film 142 is formed on the surface of a semiconductor wafer W by a chemical vapor deposition (CVD) method. Here, a thin film 144 of the bottom layer of gate electrode 146 is a gate insulation film, for example, a thermal oxide film ($SiO_2$ film) having a film thickness of about 5 nm. Impurity ions are implanted into the surface of the substrate in both sides of gate electrode 146.

The etch back process for forming the sidewall in the present embodiment includes a first etching process, as illustrated in FIG. 7(b), in which the entire surface is etched until the film thickness of remaining $SiO_2$ film 142 except for above or both sides of gate electrode 146 becomes a setting value $TH_s$ and a second etching process as illustrated in FIG. 7(c), in which the entire surface is etched until remaining $SiO_2$ film 142 is completely removed except for sidewalls 142w on both sides of gate electrode 146.

In the first etching process, for example, a strong anisotropic etching is performed by the following recipe.
Etching gas: $Ar/O_2/CH_2F_2$=1000/2/5 sccm
Pressure within chamber: 20 mTorr
Microwave power: 2000 W
High frequency bias power: 120 W In the second etching process, for example, a weak anisotropic etching is performed by the following recipe.
Etching gas: $Ar/CH_2F_2$=360/20 sccm
Pressure within chamber: 100 mTorr
Microwave power: 2000 W
High frequency bias power: 75 W In the above-described etch back process, in order to prepare an ideal sidewall structure as illustrated in FIG. 7(c) without causing recess as illustrated in FIG. 8A or footing as illustrated in FIG. 8B, film thickness setting value $TH_s$ is preferably selected to be a small dimension immediately before the substrate is exposed, for example, selected to be 1 mm.

The microwave plasma etching device of the present embodiment, when performing the two-stage etch back process as described above, detects or estimates a timing when the film thickness of $SiO_2$ film 142 reaches setting value $TH_s$ by the function of the film thickness monitoring and stops the first etching process at that timing and subsequently starts the second etching process.

In this case, optical monitor device 100 turns ON light source 130 to irradiate monitor light LB on the surface of semiconductor wafer W on susceptor 12 through monitor head 102 and optical waveguide 104 while the first etching process is being performed at the full. Further, reflected light HB from the surface of semiconductor wafer W received through optical waveguide 104 and monitor head 102 is subjected to a photoelectric conversion using light receiving unit 132 and also provided to a signal processing of monitor circuit 134. Therefore, the decrease of the film thickness of $SiO_2$ film 142 on the surface of the semiconductor wafer may be monitored in real time as the etching process time elapses.

Figure 9:
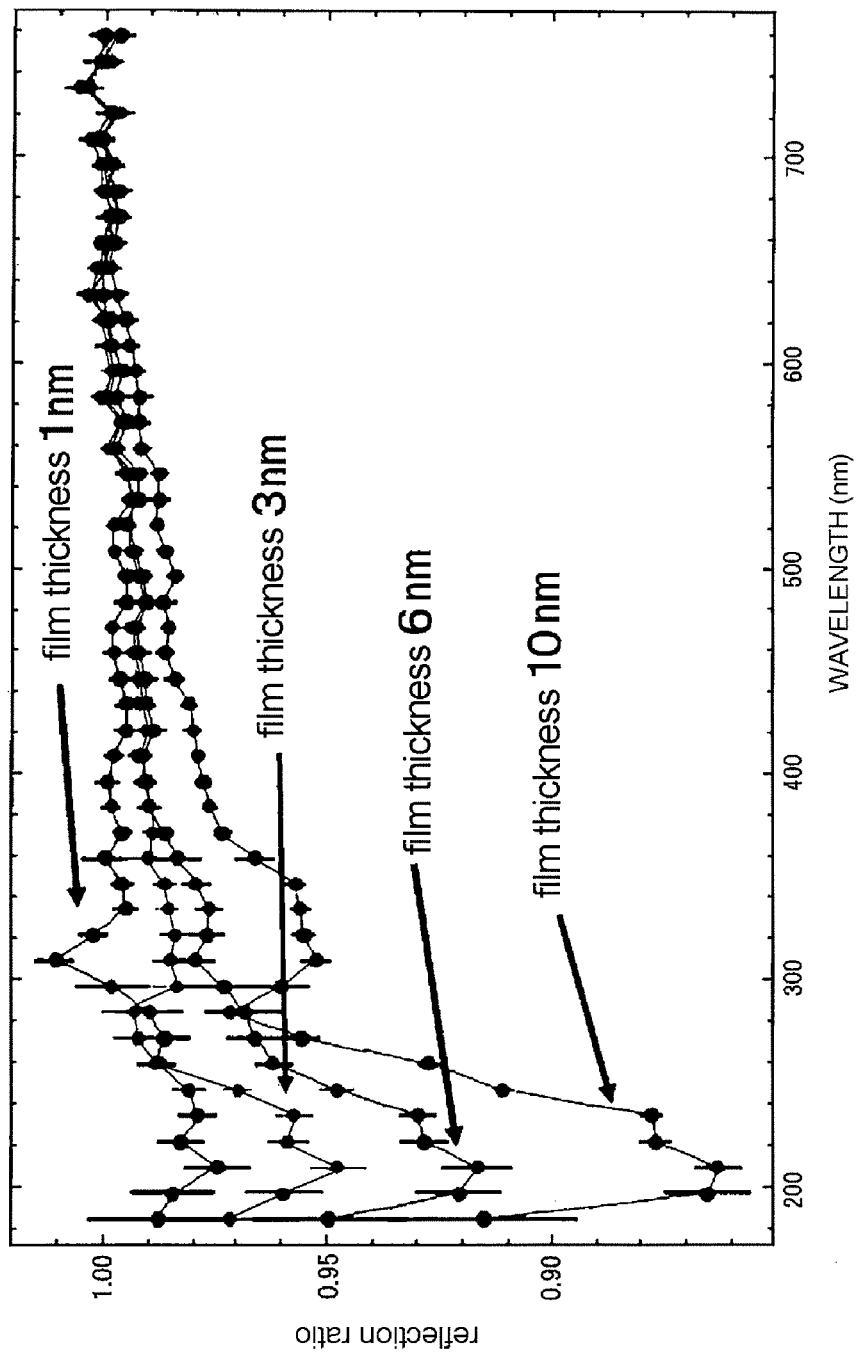
FIG. 9 is a view illustrating a wavelength dependency characteristic of reflectivity in an $SiO_2$ film.

FIG. 9 illustrates a characteristic in which a wavelength dependency characteristic of the spectrum reflection ratio of reflected light HB obtained by irradiating monitor light LB in the region of 185 nm to 785 nm on the $SiO_2$ film of the surface of semiconductor wafer W varies according to the film thickness of the $SiO_2$ film in optical monitor device 100.

As illustrated, in the case of the $SiO_2$ film, as the film thickness decreases, the reflection ratio in the entire wavelength region generally reduces, and in particular, a difference in the film thickness dependency characteristic becomes noticeable in a short wavelength region of 200 nm or less. Therefore, a timing when the film thickness of $SiO_2$ film 142 becomes setting value $TH_s$ (1 nm) may be detected or estimated based on, for example, the reflection ratio characteristic of a limited wavelength region near 200 nm or a profile (waveform) of the reflection ratio characteristic of the extensive entire wavelength region (185 nm to 785 nm).

In the present embodiment, the wavelength dependency characteristic of the reflection ratio (FIG. 9) is set to a reflection ratio which is obtained in a state where $SiO_2$ film 142 is completely exposed except for the sidewall of the gate electrode 146, i.e., in a state where the substrate (under-layer) is exposed (the state equivalent to FIG. 7(c) as the reference value. Like this, as the reflection ratio obtained at the under-layer at the time when the thin film to be etched is completely removed is set as the reference value, even a very thin film thickness of about 1 nm may be monitored with a high precision.

In the meantime, in the two-step etch back process, a timing (terminating timing detection) when the etching process is stopped may be set using, for example, a timer function or a known scheme (a light emitting monitor) which spectrumizes and detects the plasma light is may be used. In this case, optical waveguide 104 of optical monitor device 100 may be used for the window for monitoring light emission. As such, optical monitor device 100 of the present embodiment may be used in various types of film thickness monitoring or other optical monitoring.

As described above, although preferred embodiments of the present invention are described, the present invention is not limited to the embodiments described above, and other embodiments and various modifications may be made within the technical spirit and scope of the present invention.

Figure 10:
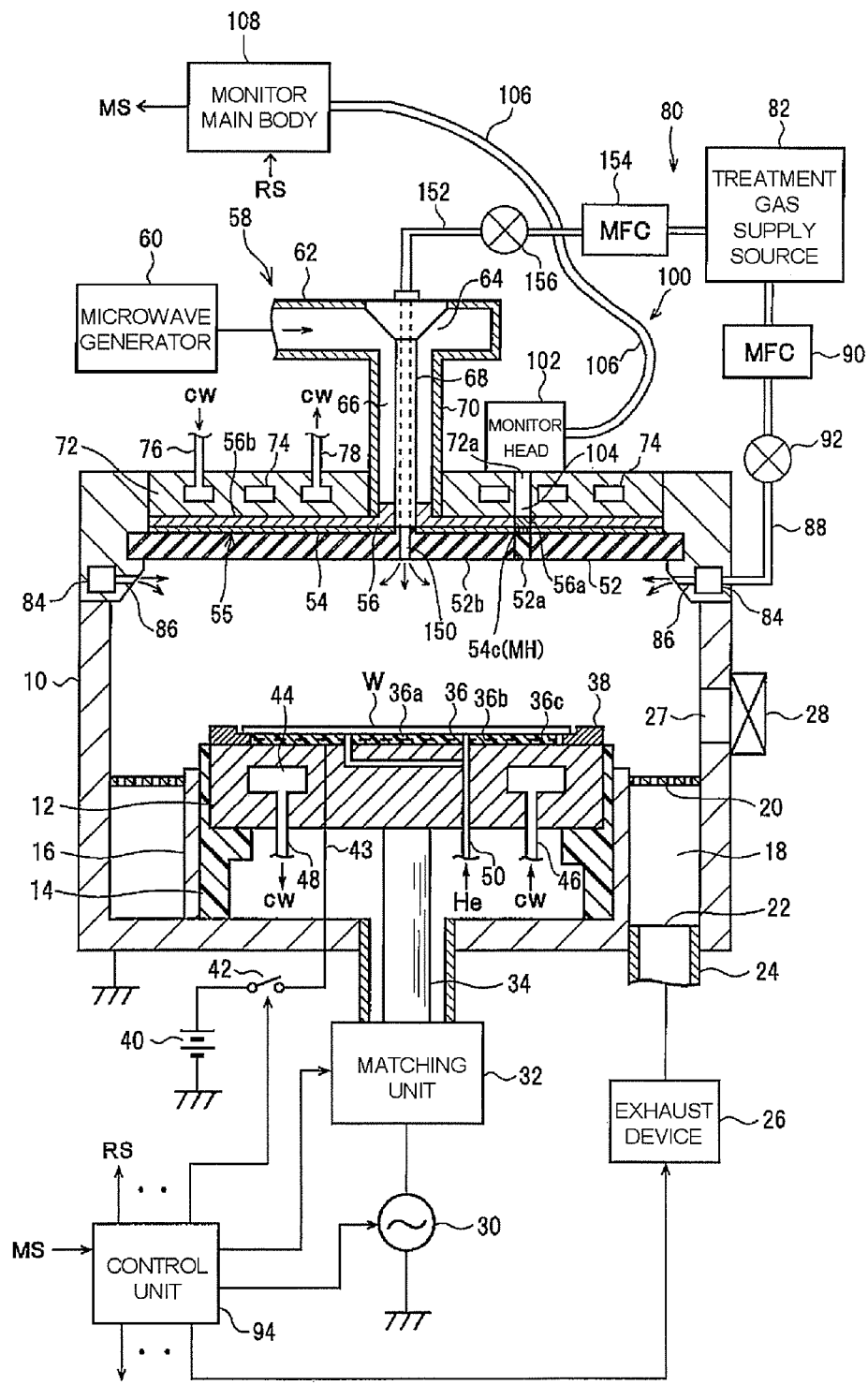
FIG. 10 is view illustrating a modified example of the plasma treatment device of FIG. 1.

For example, as illustrated in FIG. 10, internal conductor 68 of coaxial pipe 66 constituting microwave transmission line 58 may be configured by a hollow tube, and hollow tube 68 may be used for a central gas supply path of treatment gas supply unit 80. In this case, a gas ejection port 150 penetrating through the center of radial line slot antenna 55 is formed to be continued with hollow tube 68. The center of radial line slot antenna 55 is the center of the radial waveguide, and even if a through hole 150 for ejecting gas is formed at this location, the uniformity of the electromagnetic wave radiation characteristic is not affected, and further there is no conflict or contrary relationship in relation to optical monitor device 100.

In treatment gas supply unit 80 of this configuration example, a part of the treatment gas delivered from treatment gas supply source 82, as described above, passes through gas supply pipe 88 and is introduced into chamber 10 from gas ejection port 86 of the sidewall of chamber 10. Further, the other part of the treatment gas delivered from treatment gas supply source 82 passes through gas supply pipe 152 and internal conductor 68 of coaxial pipe 66, and is introduced into chamber 10 from gas ejection port 150 of the central part of the ceiling. In the meantime, a mass flow controller (MFC) 154 and an opening and closing valve 156 are installed in way of the gas supply pipe 152.

Figure 11:
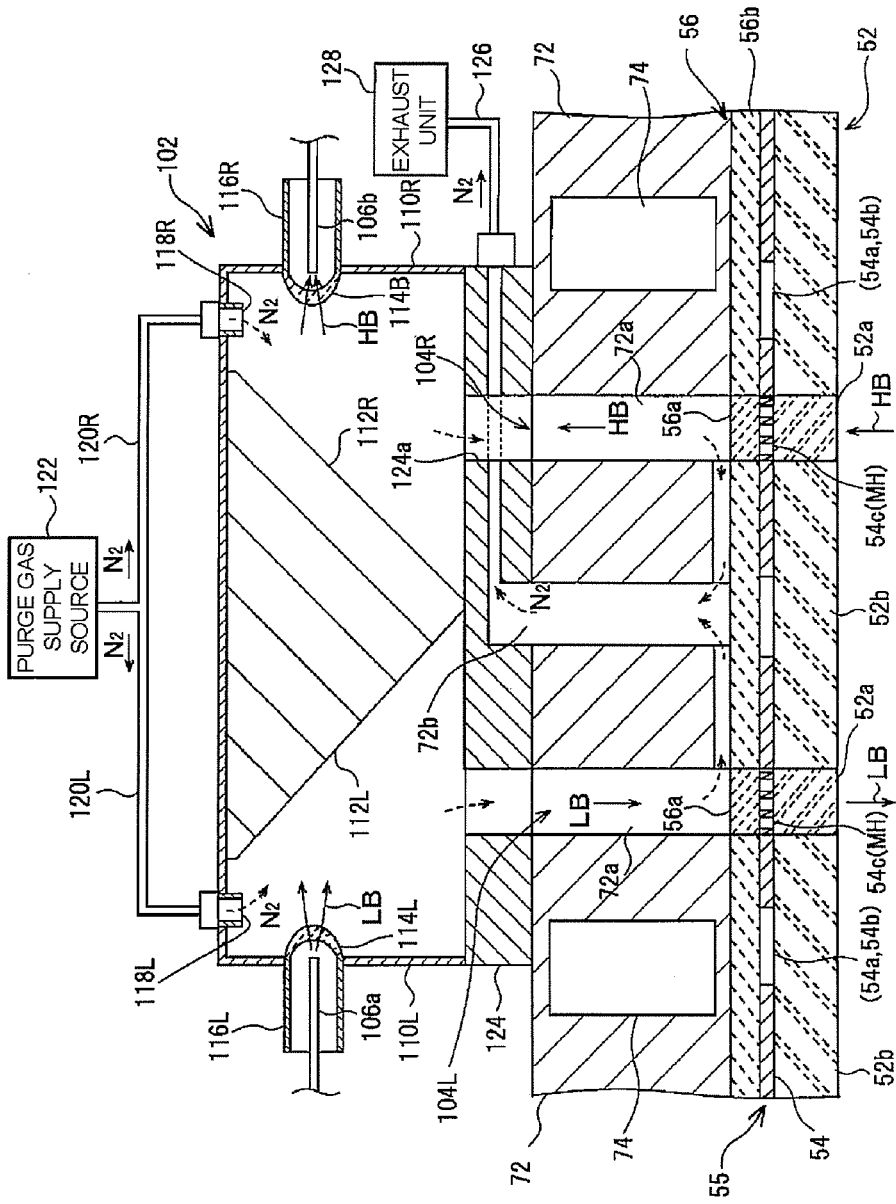
FIG. 11 is view illustrating a modified example of the optical waveguide and the monitor head in the optical monitor device of the embodiment.

Each component constituting optical monitor device 100 may also be modified in various ways. For example, as illustrated in FIG. 11, optical waveguide 104 for monitoring formed around radial line slot antenna 55 may be configured to be divided into an optical waveguide 104L for an outbound line (reserved only for monitor light LB) and an optical waveguide 104R for an inbound line (reserved only for reflected light HB). In this case, in dielectric window 52, slot plate 54, dielectric plate 56 and cover plate 72, synthetic quartz 52a, mesh type penetration holes MH, synthetic quartz 56a, and through hole 72a are individually and separately formed at a location or portion where optical waveguide 104L for the outbound line (reserved only for monitor light LB) passes and optical waveguide 104R for the inbound line (reserved only for reflected light HB) passes.

Further, in monitor head 102, optical systems 112L and 114L and housing 110L are individually allotted to optical waveguide 104L for the outbound line (reserved only for monitor light LB), and optical systems 112R and 114R and housing 110R are individually allotted to optical waveguide 104R for the outbound line (reserved only for reflected light HB).

In optical fiber 106, an outbound cable 106a is attached to housing 110L at the outbound side through a sleeve 116L made of a conductor and an inbound cable 106b is connected to housing 110R at the inbound side through a sleeve 116R made of a conductor. Further, a purge gas is supplied to housings 110L and 110R from a common purge gas supply source 122 through individual gas supply pipes 120L and 120R and gas inlet ports 118L and 118R.

In the meantime, optical waveguide 104L for the outbound line (reserved only for monitor light LB) and optical waveguide 104R for the inbound line (reserved only for reflected light HB) may be formed in a V shape obliquely inclined with respect to a vertical line, and housings 110L and 110R may be separated from each other.

Further, optical fiber 106 may be omitted and a different optical transmission system may be used between monitor head 102 and monitor body 108.

In the microwave plasma treatment device of the present embodiment, the configuration of the microwave discharge mechanism, in particular, microwave transmission line 58 and radial line microwave transmission line 55 are merely examples, and other scheme or types of microwave transmission lines and slot antenna may also be used.

In dielectric window 52 of the present embodiment, the synthetic quartz having a high transmittance to a shorter wavelength (in particular, 200 nm or less) is used at a portion 52a where optical waveguide 104 for monitoring passes. However, when monitor light LB does not include such a shorter wavelength, the fused quartz or the other transparent dielectric may be used at portion 52a where the optical waveguide passes. Further, in dielectric window 52, an alumina or non-transparent dielectric may be used in a portion except for portion 52a where optical waveguide 104 passes.

Since the microwave plasma etching device of the embodiment generates microwave plasma in non-magnetic field, it is not needed to install a magnetic field forming mechanism, such as a permanent magnet or an electromagnetic coil, at circumference of the chamber 10, so that device configuration can be simplified as much. However, the present invention may also be applied to a plasma treatment device using an electron cyclotron resonance (ECR).

INDUSTRIAL APPLICABILITY

The present invention is not limited to the microwave plasma etching device of the above-described embodiment, but may be applied to other microwave plasma treatment devices, such as plasma CVD, plasma ALD, plasma oxidation, plasma nitration, plasma doping, sputtering apparatuses. Further, the substrate to be treated in the present invention is

EXPLANATION OF SYMBOLS

| | |
|---|---|
| 10: chamber | 12: susceptor (lower electrode) |
| 26: exhaust device | |
| 30: high frequency power supply (for RF biasing) | |
| 52: dielectric window (ceiling plate) | |
| 52a: synthetic quartz (optical waveguide passing portion) | |
| 54: slot plate | 54a, 54b: a pair of slots |
| 54c: optical waveguide passing area (mesh) | MH: mesh shaped penetration hole |
| 55: radial line slot antenna | 56: dielectric plate |
| 58: microwave transmission line | 60: microwave generator |
| 66: coaxial pipe | 72: cover plate |
| 72a: through hole (optical waveguide passing portion) | |
| 80: treatment gas supply unit | |
| 94: controller | 100: optical monitor device |
| 102: monitor head | 108: monitor body |

What is claimed is:

1. A plasma treatment device comprising:
a treatment vessel that is capable of being evacuated and at least partly includes a dielectric window;
a substrate holding unit that holds a substrate to be treated within the treatment vessel;
a treatment gas supply unit that supplies a predetermined treatment gas within the treatment vessel in order to perform a predetermined plasma treatment on the substrate;
a slot plate made of a conductor that includes one or plural slots to radiate microwave within the treatment vessel, wherein the slot plate is installed above the dielectric window;
a microwave supply unit including a coaxial pipe that supplies microwave into the treatment vessel through the coaxial pipe, the slot plate and the dielectric window in order to generate plasma of the treatment gas by plasma discharge; and
an optical monitor unit disposed above the treatment vessel and that optically monitors or measures a surface of the substrate within the treatment vessel through mesh type penetration holes formed in the slot plate installed above the dielectric window,
wherein the optical monitor unit includes:
a light source that generates monitor light;
a light receiving unit that converts reflected light from the substrate for the monitor light into an electrical signal;
a monitor circuit that outputs monitor information or a monitor result by allowing the electrical signal from the light receiving unit to be subjected to a predetermined signal processing;
a monitor head that irradiates the monitor light on the surface of the substrate held on the substrate holding unit through the mesh type penetration holes of the slot plate installed above the dielectric window, and receive the reflected light from the surface of the substrate through the mesh type penetration holes of the slot plate installed above the dielectric window;
a monitor light transmission unit that transmits the monitor light from the light source to the monitor head; and
a reflected light transmission unit that transmits the reflected light from the monitor head to the light receiving unit, and
the monitor head includes:
a sealable housing that is made of a conductor and connected to an optical waveguide disposed below the sealable housing, wherein the optical waveguide traverses through the dielectric window and the mesh type penetration holes formed in the slot plate such that the monitor light and the reflected light pass between the sealable housing and the mesh type penetration holes through the optical waveguide, wherein the optical waveguide is radially separate from the coaxial pipe and does not extend into the coaxial pipe of the microwave supply unit,
a predetermined optical component that is located at a position where the monitor light or the reflected light passes within the housing,
a purge gas supply unit that supplies a purge gas into the housing, and an exhaust unit that exhausts the gas from the inside of the housing.

2. The plasma treatment device of claim 1, wherein a dielectric plate to shorten the wavelength of the microwave while propagating through the microwave from the microwave supply unit in a diametrical direction and a cover plate above the dielectric plate are installed between the monitor head and the dielectric window, and
the cover plate includes a through hole that communicates with the housing of the monitor head at a position that is overlapped with the region where the mesh shaped penetration holes of the slot plate are distributed.

3. The plasma treatment device of claim 2, wherein the purge gas supplied from the purge gas supply unit into the housing is sent to the exhaust unit through the through hole of the cover plate.

4. The plasma treatment device of claim 1, wherein the monitor circuit is connected to the monitor head via an optical fiber that does not extend into the coaxial pipe of the microwave supply unit.

5. The plasma treatment device of claim 1, wherein the mesh type penetration holes are distributed within an optical waveguide passing area of the slot plate and have a predetermined density.

6. the plasma treatment device of claim 5, wherein the optical waveguide passing area includes a light shielding part that separates each mesh type penetration hole in the optical waveguide passing area.

7. A plasma treatment device comprising:
a treatment vessel that is capable of being evacuated and at least partly includes a dielectric window;
a substrate holding unit that holds a substrate to be treated within the treatment vessel;
a treatment gas supply unit that supplies a predetermined treatment gas within the treatment vessel in order to perform a predetermined plasma treatment on the substrate;
a slot plate made of a conductor that includes one or plural slots to radiate microwave within the treatment vessel, wherein the slot plate is installed above the dielectric window;
a microwave supply unit including a coaxial pipe that supplies microwave into the treatment vessel through the coaxial pipe, the slot plate and the dielectric window in order to generate plasma of the treatment gas by plasma discharge; and an optical monitor unit disposed above the treatment vessel and that optically monitors or measures a surface of the substrate within the treatment vessel using monitor light passing through mesh type penetration holes formed in the slot plate installed above the dielectric window, wherein the optical monitor unit includes a monitor head made of a conductor and being connected to an optical waveguide disposed below the monitor head, wherein the optical waveguide traverses through the dielectric window and mesh type penetration holes formed in the slot plate such that the monitor light passes between the monitor head and the mesh type penetration holes through the optical waveguide, wherein the optical waveguide is radially separate from the coaxial pipe and does not extend into the coaxial pipe of the microwave supply unit, and wherein a top surface of a light shielding portion of the mesh type penetration holes of the slot plate is rounded.

8. The plasma treatment device of claim 7, wherein the top surface of the light shielding portion of the regions of the mesh type penetration holes is rounded by a wet etching.

9. A plasma treatment device comprising:
a treatment vessel that is capable of being evacuated and at least partly includes a dielectric window;
a substrate holding unit that holds a substrate to be treated within the treatment vessel;
a treatment gas supply unit that supplies a predetermined treatment gas within the treatment vessel in order to perform a predetermined plasma treatment on the substrate;
a slot plate made of a conductor that includes one or plural slots to radiate microwave within the treatment vessel, wherein the slot plate is installed above the dielectric window;
a microwave supply unit including a coaxial pipe that supplies microwave into the treatment vessel through the coaxial pipe, the slot plate and the dielectric window in order to generate plasma of the treatment gas by plasma discharge; and
an optical monitor unit disposed above the treatment vessel and that optically monitors or measures a surface of the substrate within the treatment vessel using monitor light passing through mesh type penetration holes formed in the slot plate installed above the dielectric window, wherein the optical monitor unit includes a monitor head made of a conductor and being connected to an optical waveguide disposed below the monitor head, wherein the optical waveguide traverses through the dielectric window and mesh type penetration holes formed in the slot plate such that the monitor light passes between the monitor head and the mesh type penetration holes through the optical waveguide, wherein the waveguide is radially separate from the coaxial pipe and does not extend into the coaxial pipe of the microwave supply unit, and wherein in the dielectric window, at least a portion that is overlapped with the region where the mesh type penetration holes of the slot plate are distributed is made of a synthetic quartz.

10. The plasma treatment device of claim 9, wherein in the dielectric window, at least a portion that is not overlapped with the region where the mesh type penetration holes of the slot plate are distributed is made of a fused quartz.

* * * * *